US012629328B2

(12) United States Patent
Jeon et al.

(10) Patent No.: US 12,629,328 B2
(45) Date of Patent: May 19, 2026

(54) OIL DISPERSION SOLID COSMETIC COMPOSITION CONTAINING ASCORBIC ACID AND PREPARATION METHOD THEREFOR

(71) Applicant: COSMAX, INC., Gyeonggi-do (KR)

(72) Inventors: Jong Hee Jeon, Gyeonggi-do (KR); Hyeon Joo Lim, Gyeonggi-do (KR); Jin Goo Ji, Gyeonggi-do (KR); Myeong Sam Park, Seoul (KR)

(73) Assignee: COSMAX, INC., Gyeonggi-do (KR)

( * ) Notice: Subject to any disclaimer, the term of this patent is extended or adjusted under 35 U.S.C. 154(b) by 845 days.

(21) Appl. No.: 17/798,726

(22) PCT Filed: Nov. 5, 2021

(86) PCT No.: PCT/KR2021/015970
§ 371 (c)(1),
(2) Date: Aug. 10, 2022

(87) PCT Pub. No.: WO2023/054795
PCT Pub. Date: Apr. 6, 2023

(65) Prior Publication Data
US 2024/0180810 A1 Jun. 6, 2024

(30) Foreign Application Priority Data
Sep. 29, 2021 (KR) ........................ 10-2021-0128937

(51) Int. Cl.
| | |
|---|---|
| *A61K 8/67* | (2006.01) |
| *A61K 8/04* | (2006.01) |
| *A61K 8/25* | (2006.01) |
| *A61K 8/60* | (2006.01) |
| *A61K 8/891* | (2006.01) |
| *A61K 8/92* | (2006.01) |
| *A61Q 19/00* | (2006.01) |

(52) U.S. Cl.
CPC ................ *A61K 8/676* (2013.01); *A61K 8/04* (2013.01); *A61K 8/25* (2013.01); *A61K 8/60* (2013.01); *A61K 8/891* (2013.01); *A61K 8/92* (2013.01); *A61K 8/922* (2013.01); *A61Q 19/00* (2013.01); *A61K 2800/10* (2013.01)

(58) Field of Classification Search
CPC ..................................................... A61K 8/676
See application file for complete search history.

(56) References Cited

FOREIGN PATENT DOCUMENTS

| | | |
|---|---|---|
| KR | 10-2007-0085734 A | 8/2007 |
| KR | 10-1151009 B1 | 6/2012 |
| KR | 10-2015-0143698 A | 12/2015 |
| KR | 10-2020-0056210 A | 5/2020 |
| KR | 2020/56210 A * 5/2020 | .............. A61K 8/31 |
| KR | 10-2140652 B1 | 8/2020 |

OTHER PUBLICATIONS

International Search Report from corresponding PCT Application No. PCT/KR2021/015970, dated Jun. 16, 2022.

* cited by examiner

*Primary Examiner* — Paul V Ward

(74) *Attorney, Agent, or Firm* — Harness, Dickey & Pierce, P.L.C.

(57) ABSTRACT
The present invention relates to an oil dispersion solid cosmetic composition containing ascorbic acid and a preparation method therefor, wherein the cosmetic composition has a stable formulation even while containing a high content of ascorbic acid, and exhibits an excellent feeling in use and spreadability, and thus can be effectively used in the preparation of a cosmetic composition.

7 Claims, No Drawings

OIL DISPERSION SOLID COSMETIC COMPOSITION CONTAINING ASCORBIC ACID AND PREPARATION METHOD THEREFOR

CROSS-REFERENCE TO RELATED APPLICATIONS

This application is a national phase application of PCT Application No. PCT/KR2021/015970, filed on Nov. 5, 2021, which claims priority to Korean Patent Application No. 10-2021-0128937, filed on Sep. 29, 2021. The entire disclosure of the applications identified in this paragraph are incorporated herein by references.

TECHNICAL FIELD

The present disclosure relates to an oil dispersion solid cosmetic composition containing ascorbic acid and a preparation method therefor.

BACKGROUND ART

Ascorbic acid, also called vitamin C, is a kind of carbohydrate that is synthesized from a carbohydrate precursor, such as glucose or galactose. Since ascorbic acid is not synthesized by itself in the body, the supplementation through food is needed to prevent disease, such as scurvy, caused by a deficiency in ascorbic acid. As ascorbic acid was revealed to alleviate skin pigmentation by inhibiting melanogenesis through tyrosinase activity and to slow skin aging by promoting collagen protein synthesis and reducing reactive oxygen species in the body, the application range of ascorbic acid has been expanded from medical uses for treating deficiency syndromes, such as scurvy, to cosmetic uses for supporting skin whitening and anti-aging.

Ascorbic acid is not easy to stabilize since ascorbic acid is easily oxidized by sensitively responding to water and air, especially, oxygen and heat, and an external environment, such as light. In the conventional art, an ascorbic acid component was dissolved in an aqueous phase, such as water or a polyol, and this was stabilized by application to W/O emulsions, liposomes, or multi-emulsion systems.

However, as for W/O, a water-soluble component is dissolved in an aqueous phase, resulting in the oxidation of ascorbic acid, thereby causing a deterioration in stability and a decrease in titer. In addition, ascorbic acid may be oxidized very quickly when dissolved in water, and ascorbic acid may be inevitably affected by oxidation due to a polyol containing moisture when dissolved in the polyol, and in order to formulate the solution dissolved in the polyol into an emulsification product, water needs to be again used, and thus the titer of ascorbic acid may be inevitably unstable.

A method wherein the water-soluble ascorbic acid is allowed to dissolve in an oil phase by chemical combination with a fat-soluble component and then applied to a cosmetic product has very low efficiency in terms of unit cost, resulting in very low utilization. In particular, such a method has a great negative effect on formulation stability upon high-content mixing.

Additionally, oil dispersion solid cosmetic materials have advantages of helping moisturize the skin by forming an oil film through mixing with a high-content oil when applied to the skin, but have disadvantages of being remarkably slowly absorbed into the skin, being greasy, due to oil, by a reflection light, and being easily smeared.

Therefore, there is a need to develop a new raw material and cosmetic composition that can be stabilized even while containing a high content of ingredient, which causes contact irritation and has a decreased titer by dissolution in a water-soluble ingredient.

DISCLOSURE OF INVENTION

Technical Problem

The present inventors prepared an oil dispersion solid cosmetic composition containing ascorbic acid and, as a result of investigating an optimum mixing ratio therefor, confirmed that such a cosmetic composition has a stable formulation even while containing a high content of ascorbic acid, and exhibits excellent feeling in use and spreadability.

In accordance with an aspect of the present disclosure, there is provided an oil dispersion solid cosmetic composition containing 20.0 to 40.0 wt % of ascorbic acid, 0.1 to 3.0 wt % of a dispersant, 2.0 to 15.0 wt % of a wax, 2.0 to 10.0 wt % of a silicone powder, and 40.0 to 70.0 wt % of an oil.

In accordance with another aspect of the present disclosure, there is provided a method for preparing an oil dispersion solid cosmetic composition containing ascorbic acid, the method including:

a first mixing step of mixing ascorbic acid, a dispersant, a wax, and an oil to prepare a mixture; and a second mixing step of adding a silicone powder to the mixture, followed by mixing.

Solution to Problem

The present disclosure relates to an oil dispersion solid cosmetic composition containing ascorbic acid and a preparation method therefor, and the cosmetic composition of the present disclosure has a stable formulation even while containing a high content of ascorbic acid, and exhibits an excellent feeling in use and spreadability.

The present inventors derived an oil dispersion solid cosmetic composition, which has a stable formulation and smooth applicability even with a high content of ascorbic acid and has a differentiated feeling in use by a non-greasy and soft finish.

Hereinafter, the present disclosure will be described in more detail.

An aspect of the present disclosure provides an oil dispersion solid cosmetic composition containing 20.0 to 40.0 wt % of ascorbic acid, 0.1 to 3.0 wt % of a dispersant, 2.0 to 15.0 wt % of a wax, 2.0 to 10.0 wt % of a silicone powder, and 40.0 to 70.0 wt % of an oil.

In the present disclosure, the composition may preferably contain ascorbic acid in a content of 20.0 to 35.0 wt %, 20.0 to 30.0 wt %, 20.0 to 28.0 wt %, 20.0 to 26.0 wt %, 24 to 40 wt %, 24 to 35 wt %, 24 to 30 wt %, or 24.0 to 28.0 wt %, and for example, may contain 24.0 to 26.0 wt %, but is not limited thereto.

In the present disclosure, the composition may preferably contain the dispersant in a content of 0.1 to 2.0 wt %, 0.1 to 1.0 wt %, 0.5 to 3.0 wt %, or 0.5 to 2.0 wt %, and for example, may contain 0.5 to 1.0 wt %, but is not limited thereto.

The dispersant may be at least one selected from the group consisting of sorbitan isostearate, sorbitan sesquioleate, PEG-10 dimethicone, lauryl PEG-9 polydimethylsiloxyethyl dimethicone, cetyl PEG/PpG-10/1 dimethicone, polyglyceryl-3 polydimethylsiloxyethyl dimethicone, polyglyceryl-4 isostearate, polyglyceryl-4 diisostearate/polyhydroxystearate/sebacate, polyglyceryl-2 dipolyhydroxystearate, and polyhydroxystearic acid, and for example, may be sorbitan isostearate, but is not limited thereto.

In the present disclosure, the composition may preferably contain the wax in a content of 2.0 to 13.0 wt %, 2.0 to 12.0 wt %, 2.0 to 11.0 wt %, 7.0 to 15.0 wt %, 7.0 to 13.0 wt %, 7.0 to 12.0 wt %, 7.0 to 11.0 wt %, 9.0 to 15.0 wt %, 9.0 to 13.0 wt %, or 9.0 to 12.0 wt %, and for example, may contain 9.0 to 11.0 wt %, but is not limited thereto.

The wax may be at least one selected from the group consisting of polyethylene, paraffin, microcrystalline wax, ceresin, candelilla wax, carnauba wax, beeswax, ozokerite, and synthetic wax, and for example, may be at least one selected from the group consisting of polyethylene, paraffin, and microcrystalline wax, but is not limited thereto.

In the present disclosure, the composition may preferably contain the silicone powder in a content of 2.0 to 9.0 wt %, 2.0 to 8.0 wt %, 3.0 to 10.0 wt %, 3.0 to 9.0 wt %, 3.0 to 8.0 wt %, 5.0 to 10.0 wt %, 5.0 to 9.0 wt %, 5.0 to 8.0 wt %, 7.0 to 10.0 wt %, or 7.0 to 9.0 wt %, and for example, may contain 7.0 to 8.0 wt %, but is not limited thereto.

The silicone powder may be at least one selected from the group consisting of polymethylsilsesquioxane, vinyl dimethicone/methicone silsesquioxane crosspolymer, silica, silica silylate, silica dimethylsilylate, elastomer, dimethicone/dimethicone crosspolymer, diphenyl dimethicone/vinyl diphenyl dimethicone/silsesquioxane crosspolymer, dimethicone/vinyl dimethicone crosspolymer, polysilicon-1 crosspolymer, polysilicon-11, and polysilicon-22, and for example, may be at least one selected from the group consisting of polymethylsilsesquioxane, vinyl dimethicone/methicone silsesquioxane crosspolymer, silica, silica silylate, and silica dimethylsilylate, but is not limited thereto.

In the present disclosure, the composition may preferably contain the oil in a content of 40.0 to 65.0 wt %, 40.0 to 60.0 wt %, 40.0 to 55.0 wt %, 45.0 to 70.0 wt %, 45.0 to 65.0 wt %, 45.0 to 60.0 wt %, 45.0 to 55.0 wt %, 50.0 to 70.0 wt %, 50.0 to 65.0 wt %, or 50.0 to 60.0 wt %, and for example, may contain 50.0 to 55.0 wt %, but is not limited thereto.

The oil may be at least one selected from the group consisting of cetyl ethylhexanoate, a hydrogenated vegetable oil, triethylhexanoin, diisostearyl malate, dimethicone as a silicone oil, phenyl trimethicone, diphenylsiloxyphenyltrimethicone, cyclomethicone, methyl trimethicone, cyclohexasiloxane, caprylyl methicone, diphenyl dimethicone, cyclopentasiloxane, cyclopentasiloxane, trisiloxane, and dimethiconol, and for example, may be at least one selected from the group consisting of cetyl ethylhexanoate, a hydrogenated vegetable oil, triethylhexanoin, diisostearyl malate, VP/hexadecene copolymer, and dimethicone as a silicone oil, and phenyl trimethicone, but is not limited thereto.

In the present disclosure, the composition may contain a silicone oil as a part of the oil, and therefore, the composition may contain the silicone oil in a content of 10.0 to 18.0 wt %, 10.0 to 16.0 wt %, 10.0 to 14.0 wt %, 12.0 to 20.0 wt %, 12.0 to 18.0 wt %, 12.0 to 16.0 wt %, 12.0 to 14.0 wt %, 14.0 to 20.0 wt %, or 14.0 to 18.0 wt %, and for example, may contain 14.0 to 16.0 wt %, but is not limited thereto.

In the present disclosure, the composition may further contain a film former, and the film former may be a VP/hexadecene copolymer, but is not limited thereto.

In the present disclosure, the composition may further contain a preservative, and the preservative may be caprylyl glycol, but is not limited thereto.

In an embodiment of the present disclosure, the oil dispersion cosmetic composition may contain 26.0 wt % of ascorbic acid, 1.0 wt % of a dispersant, 11.0 wt % of a wax, 7.1 wt % of a silicone powder, and 54.35 wt % of an oil, and a part of the oil may be 14.0 wt % of a silicone oil relative to the total oil dispersion cosmetic composition.

Another aspect of the present disclosure is a method for preparing an oil dispersion solid cosmetic composition containing ascorbic acid, the method including:

a first mixing step of mixing ascorbic acid, a dispersant, a wax, and an oil to prepare a mixture; and a second mixing step of adding a silicone powder to the mixture, followed by mixing.

In the present disclosure, the first mixing step and the second mixing step may be independently performed in a temperature condition of 60 to 100° C., and may be performed in a temperature condition of, preferably, 60 to 95° C., 60 to 90° C., 60 to 85° C., 65 to 100° C., 65 to 95° C., 65 to 90° C., 65 to 85° C., 70 to 100° C., 70 to 95° C., 70 to 90° C., 70 to 85° C., 75 to 100° C., 75 to 95° C., or 75 to 90° C., and for example, 75 to 85° C., but is not limited thereto.

In the present disclosure, in the second mixing step, a mixture may be prepared containing 20.0 to 40.0 wt % of ascorbic acid, 0.1 to 3.0 wt % of the dispersant, 2.0 to 15.0 wt % of the wax, 2.0 to 10.0 wt % of the silicone powder, and 40.0 to 70.0 wt % of the oil.

Advantageous Effects of Invention

The present disclosure is directed to an oil dispersion solid cosmetic composition containing ascorbic acid and a preparation method therefor, wherein the cosmetic composition has a stable formulation even while containing a high content of ascorbic acid, and exhibits an excellent feeling in use and spreadability, and thus can be effectively used in the preparation of a cosmetic composition.

BEST MODE FOR CARRYING OUT THE INVENTION

The present disclosure relates to an oil dispersion solid cosmetic composition containing 20.0 to 40.0 wt % of ascorbic acid, 0.1 to 3.0 wt % of a dispersant, 2.0 to 15.0 wt % of a wax, 2.0 to 10.0 wt % of a silicone powder, and 40.0 to 70.0 wt % of an oil.

MODE FOR CARRYING OUT THE INVENTION

Hereinafter, the present disclosure will be described in more detail by the following exemplary embodiments. However, these exemplary embodiments are used only for illustration, and the scope of the present disclosure is not limited by these exemplary embodiments.

Throughout the present specification, the "%" used to express the concentration of a specific material, unless otherwise particularly stated, refers to (wt/wt) % for solid/solid, (wt/vol) % for solid/liquid, and (vol/vol) % for liquid/liquid.

Preparation Example 1: Preparation of Oil Dispersion Solid Cosmetic Compositions Examples 1 and 2 and Comparative Examples 1 and 2 were prepared by varying the types and contents of respective ingredients as shown in Table 1 below.

Specifically, all the raw materials except for silicone powders shown in Table 1 were weighed in beakers according to respective ingredients and contents thereof, and then uniformly mixed at 25 rpm for 5 minutes by an Agi-Mixer while warmed at 75 to 85° C.

Thereafter, the silicone powders were sequentially added, and uniformly mixed at 25 rpm for 5 minutes by an Agi-Mixer while warmed at 75 to 85° C. The reason is that the raw materials may be burned if the organic-based powders agglomerate to adhere to the bottoms of the beakers. Finally, air bubbles were removed, and the mixtures were poured into containers and cooled to prepare stick-shaped oil dispersion cosmetic compositions of Examples 1 and 2 and Comparative Examples 1 and 2.

TABLE 1

| | | Content (wt %) | | | |
|---|---|---|---|---|---|
| Classification | Ingredient name | Example 1 | Example 2 | Comparative Example 1 | Comparative Example 2 |
| — | Ascorbic acid | 26.00 | 26.00 | 26.00 | 26.00 |
| Oil | cetyl ethylhexanoate | 16.10 | 16.13 | 16.13 | 16.13 |
| | hydrogenated vegetable oil | 14.90 | 14.87 | 14.87 | 14.87 |
| | triethylhexanoin | 4.95 | 5.04 | 12.04 | 4.95 |
| | diisostearyl malate | 4.40 | 9.41 | 4.41 | 10.50 |
| Silicone oil | dimethicone | 9.00 | 9.00 | 9.00 | 9.00 |
| | phenyl trimethicone | 5.00 | 5.00 | 5.00 | 5.00 |
| Wax | polyethylene | 4.50 | 4.50 | 4.50 | 4.50 |
| | paraffin | 4.05 | 4.05 | 4.05 | 4.05 |
| | microcrystalline wax | 2.45 | 3.45 | 2.45 | 3.45 |
| Silicone powder | polymethylsilsesquioxane | 2.30 | — | — | — |
| | vinyl dimethicone/methicone silsesquioxane crosspolymer | 2.00 | — | — | — |
| | silica | 1.20 | — | — | — |
| | silica silylate | 1.00 | — | — | — |
| | silica dimethylsilylate | 0.60 | 1.00 | — | 1.00 |
| Dispersant | sorbitan isostearate | 1.00 | 1.00 | 1.00 | — |
| Film former | VP/hexadecene copolymer | 0.50 | 0.50 | 0.50 | 0.50 |
| Preservative | caprylyl glycol | 0.05 | 0.05 | 0.05 | 0.05 |

Test Example 1: Formulation Stability of Cosmetic Compositions

When a high content of ascorbic acid is applied to an oil dispersion solid cosmetic composition, the most important characteristic that the composition needs to have is formulation stability. The cosmetic compositions prepared in Preparation Example 1 were investigated for formulation stability according to the following test conditions.

Each of the cosmetic compositions was stored for 3 months under conditions of −4° C., 25° C., 37° C., 45° C., and cycling (the storage temperature was changed to −4° C. and 45° C. three times every 24 hours) and exposure to sunlight, and then was observed for stability changes. The results are shown in Table 2 below (◎: stable, Δ: slight unstable, X: unstable, -: no performed).

TABLE 2

| | | Examplex 1 | Example 2 | Comparative Example 1 | Comparative Example 2 |
|---|---|---|---|---|---|
| 1 Day | −4° C. | ◎ | ◎ | X | ◎ |
| | 25° C. | ◎ | ◎ | X | ◎ |
| | 37° C. | ◎ | ◎ | X | ◎ |
| | 45° C. | ◎ | ◎ | X | ◎ |
| | Cycling | ◎ | ◎ | X | ◎ |
| | Exposure to sunlight | ◎ | ◎ | X | ◎ |

TABLE 2-continued

| | | Examplex 1 | Example 2 | Comparative Example 1 | Comparative Example 2 |
|---|---|---|---|---|---|
| 1 Week | −4° C. | ◎ | ◎ | — | Δ |
| | 25° C. | ◎ | ◎ | — | Δ |
| | 37° C. | ◎ | ◎ | — | Δ |
| | 45° C. | ◎ | ◎ | — | Δ |
| | Cycling | ◎ | ◎ | — | Δ |
| | Exposure to sunlight | ◎ | ◎ | — | Δ |

TABLE 2-continued

| | | Examplex 1 | Example 2 | Comparative Example 1 | Comparative Example 2 |
|---|---|---|---|---|---|
| 1 Month | −4° C. | ◎ | ◎ | — | X |
| | 25° C. | ◎ | ◎ | — | X |
| | 37° C. | ◎ | ◎ | — | X |
| | 45° C. | ◎ | ◎ | — | X |
| | Cycling | ◎ | ◎ | — | X |
| | Exposure to sunlight | ◎ | ◎ | — | X |
| 2 Months | −4° C. | ◎ | ◎ | — | X |
| | 25° C. | ◎ | ◎ | — | X |
| | 37° C. | ◎ | ◎ | — | X |
| | 45° C. | ◎ | ◎ | — | X |
| | Cycling | ◎ | ◎ | — | X |
| | Exposure to sunlight | ◎ | ◎ | — | X |
| 3 Months | −4° C. | ◎ | ◎ | — | X |
| | 25° C. | ◎ | ◎ | — | X |
| | 37° C. | ◎ | ◎ | — | X |
| | 45° C. | ◎ | ◎ | — | X |
| | Cycling | ◎ | ◎ | — | X |
| | Exposure to sunlight | ◎ | ◎ | — | X |

As can be confirmed in Table 2, Comparative Example 1 was observed to be unstable, for example, agglomeration and precipitation of ascorbic acid, while filled and cooled in the container after preparation. Similarly, Comparative Example 2 was also observed to be unstable, for example, agglomeration and precipitation of ascorbic acid, one week after preparation. However, Examples 1 and 2 showed favorable formulation stability even 3 months after preparation.

Test Example 2: Ascorbic Acid Titers of Cosmetic Composition

Example 1 prepared in Preparation Example 1 was investigated for titers through analysis of ascorbic acid contents according to the following experimental conditions.

TABLE 3

| | | Analysis results | |
|---|---|---|---|
| Storage conditions | Change over time | Content (wt %) | Conservation (%) |
| Room temperature | Initial | 25.16 | 96.77 |
| Room temperature | 1 Week | 23.91 | 91.96 |
| 45° C. | | 23.69 | 91.12 |
| Exposure to sunlight | | 24.55 | 94.42 |
| Room temperature | 1 Month | 23.54 | 90.54 |
| 45° C. | | 23.39 | 89.96 |
| Exposure to sunlight | | 23.78 | 91.46 |
| Room temperature | 2 Months | 24.92 | 95.85 |
| 45° C. | | 25.25 | 97.12 |
| Exposure to sunlight | | 23.97 | 92.19 |
| Room temperature | 3 Months | 25.23 | 97.04 |
| 45° C. | | 25.03 | 96.27 |
| Exposure to sunlight | | 25.22 | 97.00 |

As can be confirmed in Table 3, the contents of ascorbic acid were maintained at 90% or more compared with the existing one up to 3 months even by storage under room temperature, 45° C., and exposure to sunlight.

Test Example 3: Feeling in Use of Cosmetic Composition Confirmed by Sensory Evaluation Although it is important to investigate available skin improvement effects of cosmetic compositions, subjective sensory characteristics, such as a feeling in use, are also very important factors for commercialization of the cosmetic compositions. Therefore, the compositions in the preparative example were evaluated according to a 5-point scale method on 20 women in their 20s to 40s who mainly used cosmetics.

Specifically, the cosmetic compositions prepared in Preparative Example 1 were evaluated for a feeling in use, spreadability, absorbability, stickiness, and reflection light according to the following criteria (1: very bad, 2: bad, 3: medium, 4: good, 5: very good).

1) Feeling in use: The feeling of touching the face upon use of a cosmetic material was evaluated, wherein an evaluator was guided to subtract points when having a feeling of difference.

2) Spreadability: The prepared cosmetic material is a stick-shaped cosmetic material, and thus an evaluator was guided to the item for evaluating whether a cosmetic material was smoothly spread when applied to the face.

3) Absorbability: An evaluator was guided to the item for evaluating whether the evaluator had a residual feeling on the face when a cosmetic material applied to the face was absorbed. The less the residual feeling, the higher the score was given.

4) Stickiness: An evaluator was guided to the item for evaluating whether hairs or the like stuck to the face after a cosmetic material applied to the face was absorbed. The less the stickiness, the higher the score was given.

5) Reflection light: An evaluator was guided to the item for evaluating whether the face was greasy by reflection light after a cosmetic material was applied to the face. The less the greasiness, the higher the score was given.

TABLE 4

| | Example 1 | Example 2 | Comparative Example 2 |
|---|---|---|---|
| Feeling in use | 4.5 | 4.7 | 3.8 |
| Spreadability | 4.4 | 4.6 | 3.9 |
| Absorbability | 4.8 | 4.5 | 1.7 |
| Stickiness | 4.8 | 4.1 | 1.4 |
| Reflection light | 4.7 | 4.5 | 1.1 |

As can be confirmed in Table 4, Examples 1 and 2 were superior to Comparative Example 2 in the evaluation of all of the feeling in use, spreadability, absorbability, stickiness, and reflection light. Especially, almost all the evaluators felt that Example 1 was overall more satisfactory than Example 2. Comparative Example 2 was significantly lower than Examples 1 and 2 in terms of absorbability, stickiness, and reflection light, and it could be confirmed that there was an excellent effect as a cosmetic composition only when all of the ingredients included in Example 1 were contained.

INDUSTRIAL APPLICABILITY

The present disclosure relates to an oil dispersion solid cosmetic composition containing ascorbic acid and a preparation method therefor.

What is claimed is:

1. A solid cosmetic composition in the form of an oil dispersion comprising:
   24.0 to 40.0 wt % of ascorbic acid;
   0.1 to 3.0 wt % of a dispersant;
   2.0 to 15.0 wt % of a wax;
   2.0 to 10.0 wt % of a silicone powder; and
   40.0 to 60.0 wt % of an oil,
   wherein all weight percentages are based on the total weight of the composition.

2. The composition of claim 1, wherein the dispersant is selected from the group consisting of sorbitan isostearate, sorbitan sesquioleate, PEG-10 dimethicone, lauryl PEG-9 polydimethylsiloxyethyl dimethicone, cetyl PEG/PpG-10/1 dimethicone, polyglyceryl-3 polydimethylsiloxyethyl dimethicone, polyglyceryl-4 isostearate, polyglyceryl-4 diisostearate/polyhydroxystearate/sebacate, polyglyceryl-2 dipolyhydroxystearate, and polyhydroxystearic acid.

3. The composition of claim 1, wherein the wax is selected from the group consisting of polyethylene, paraffin, microcrystalline wax, ceresin, candelilla wax, carnauba wax, beeswax, ozokerite, and synthetic wax.

4. The composition of claim 1, wherein the silicone powder is selected from the group consisting of polymethylsilsesquioxane, vinyl dimethicone/methicone silsesquioxane crosspolymer, silica, silica silylate, silica dimethylsilylate, elastomer, dimethicone/dimethicone crosspolymer, diphenyl dimethicone/vinyl diphenyl dimethicone/silsesquioxane crosspolymer, dimethicone/vinyl dimethicone crosspolymer, polysilicon-1 crosspolymer, polysilicon-11, and polysilicon-22.

5. The composition of claim 1, wherein the oil is selected from the group consisting of cetyl ethylhexanoate, a hydrogenated vegetable oil, triethylhexanoin, diisostearyl malate, dimethicone, phenyl trimethicone, diphenylsiloxyphenylt-rimethicone, cyclomethicone, methyl trimethicone, cyclo-hexasiloxane, caprylyl methicone, diphenyl dimethicone, cyclopentasiloxane, trisiloxane, and dimethiconol.

6. A method for preparing a solid cosmetic composition in the form of an oil dispersion containing ascorbic acid, the method comprising:

a first mixing step of mixing ascorbic acid, a dispersant, a wax, and an oil to prepare a mixture; and a second mixing step of adding a silicone powder to the first mixture, followed by mixing, wherein the composition prepared in the second mixing step comprises:

24.0 to 40.0 wt % of ascorbic acid;

0.1 to 3.0 wt % of a dispersant;

2.0 to 15.0 wt % of a wax;

2.0 to 10.0 wt % of a silicone powder; and 40.0 to 60.0 wt % of an oil, wherein all weight percentages are based on the total weight of the composition.

7. The method of claim 6, wherein the first mixing step and the second mixing step are each performed at a temperature condition of 60 to 100° C.

* * * * *